(12) United States Patent
Kim et al.

(10) Patent No.: US 6,573,388 B1
(45) Date of Patent: Jun. 3, 2003

(54) ETHYLAZIRIDINE DERIVATIVES AND THEIR PREPARATION METHODS

(75) Inventors: Byung Moon Kim, Kwachon (KR); Sung Jin Bae, Seoul (KR); Soon Mok So, Jonju (KR); Jae Sung Kang, Yongin (KR); Joong Hwan Lee, Seoul (KR)

(73) Assignee: Samchully Pharm. Co., Ltd. (KR)

( * ) Notice: Subject to any disclaimer, the term of this patent is extended or adjusted under 35 U.S.C. 154(b) by 0 days.

(21) Appl. No.: 10/069,318

(22) PCT Filed: Aug. 10, 2000

(86) PCT No.: PCT/KR00/00876

§ 371 (c)(1),
(2), (4) Date: Feb. 18, 2002

(87) PCT Pub. No.: WO01/12599

PCT Pub. Date: Feb. 22, 2001

(30) Foreign Application Priority Data

Aug. 18, 1999 (KR) .............................. 99-34142

(51) Int. Cl.$^7$ .............................. C07D 203/04
(52) U.S. Cl. ................ 548/965; 548/967; 548/968; 548/969
(58) Field of Search ................ 548/965, 967, 548/968, 969

(56) References Cited

U.S. PATENT DOCUMENTS

| | | |
|---|---|---|
| 3,890,302 A | 6/1975 | Kotera et al. |
| 5,112,990 A | 5/1992 | Sharpless et al. |
| 5,484,926 A | 1/1996 | Dressman et al. |

OTHER PUBLICATIONS

Tetrahedron Letter, vol. 32, No. 16, pp. 1897–1898 (1991).

Synlett, vol. 6, pp. 527–529 (1992).

J. Chem. Soc. Perkin Trans. 1, vol. 21, 2863–2870 (1992).

International Search Report for PCT/KR00/00876, Korean Industrial Property Office, Nov. 24, 2000.

*Primary Examiner*—Joseph K. McKane
*Assistant Examiner*—Andrea D. Small
(74) *Attorney, Agent, or Firm*—Harness, Dickey & Pierce, P.L.C.

(57) ABSTRACT

This invention is related to new ethylaziridine derivatives of formula (I) and their preparation. The compounds are useful synthetic intermediates for the synthesis of HIV protease inhibitors and oligopeptide mimetics.

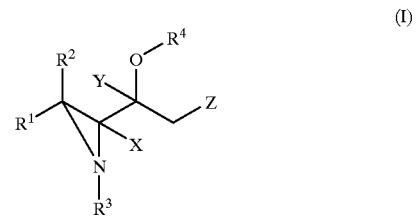

(I)

2 Claims, No Drawings

ETHYLAZIRIDINE DERIVATIVES AND THEIR PREPARATION METHODS

This application is a 371 of PCT/KR00/00876 Aug. 10, 2000.

FIELD OF THE INVENTION

This invention is related to new ethylazindine derivatives and their preparation. The compounds are useful synthetic intermediates for the synthesis of HIV protease inhibitors and oligopeptide mimetics.

BACKGROUND OF THE INVENTION

HIV is a retrovirus delivering the genetic information in the form of RNA. Therapeutic agents for the virus include reverse transcriptase inhibitors and HIV protease inhibitors, which do not kill the virus in cells, rather inhibit the replication of the virus. Moreover, rapid emergence of viral strains resistant against the chemotherapeutics requires development of therapeutic agents of new structure.

HIV protease inhibitors which have been developed so far include Roche's Saquinavir [EP 432695 A (1991)], Glaxo-Weilcome's Amprenavir [U.S. Pat. No. 941,982 (1992)], Merck's Indinavir [U.S. Pat. No. 789,508 (1991)]. Abbott's Ritronavir [U.S. Pat. No. 998,114 (1992)], and Agouron's Nelfinavir [U.S. Pat. No. 5,484,926 (1996)]. These compounds are used for the prevention or treatment of AIDS caused by HIV viral infection.

Most of these HIV protease inhibitors belong to the hydroxyethylamine (HEA) class inhibitors. Except Nelfinavir, Saquinavir, Palinavir, and Amorenavir have benzyl group at the C(2) of the hydroxyethylamine backbone.

Intermediates for the synthesis of HIV protease inhibitors reported so far are (2R)-[1'(S)-azido-2-phenylethyl]oxirane (J. Med. Chem. 1993, 36, 292–294) and 3(S)-amino-1,2(S)-epoxy-4-phenylbutane. However, these intermediates are normally derived from phenylaianine and inevitably installs benzyl group onto the backbone of the HEA backbone. On the other hand, Nelfinavir possesses phenylthiomethyl group instead of the benzyl one onto the HEA backbone, thus requires a different intermediate such as 3(S)-amino-1,2(S)-epoxy-4-phenyl thiobutane.

Therefore, a new-intermediate is required for the introduction of benzyl as well as phenylthiomethyl or other substituents for the development of new HIV protease inhibitors.

The object of this invention is to provide a new ethylaziridine derivative which is capable of introducing various substituents. Another object of this invention is to provide important intermediates for the synthesis of HIV protease inhibitors.

DETAILED DESCRIPTION OF THE INVENTION

The present invention is concerned with the ethylaziridine derivatives of formula I and their preparation methods. The new ethylaziridine derivatives are prepared from tartaric acid with amino and alcohol groups protected and the termini substituted with halogen and alkoxy groups. These aziridine derivatives can be utilized as core intermediates for the preparation of HIV protease inhibitors.

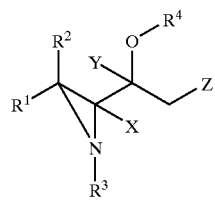
(I)

In the formula above,
$R_1$ and $R_2$ are respetively, H, alkyl, aryl, arylalkyl, or heteroatom which is bound to an alkyl, aryl or arylakyl group;
$R_3$ is H, alkyl, aryl, arylakyl, or amino protecting group forming $C_{5-7}$ monocyclic heterocycle or $C_{7-11}$ bicyclic heterocycle with nitrogen atom;
X and Y are respetively, H, $C_{1-4}$ alkyl, arylalkyl, aryl, or heteroatom which is bound to alkyl, aryl or arylakyl;
$R_4$ is silyl protecting group optionally substituted with alkyl group, or alcohol protecting group which includes alkoxycarbonyl, aryloxycarbonyl, methoxymethyl, tetrahydropyranyl, methoxyethoxy methyl or ethoxyvinylethyl;
Z is F, Cl, Br, I, or $-OR_5$; and
$R_5$ is $SO_nR_6$, where n=0, 1 or 2, and $R_6$ is alkyl or aryl.

The synthetic method for ethylaziridine derivatives of general formula (I') where $R_1$, $R_2$, X and Y are H is as follows.

In the case where tartaric acid is used as a starting material:

(1) D-methyl tartrate is prepared from the reaction of D-tartaric acid and $SOCl_2$ in methanol.

(2) 4,5-Dimethoxycarbonyl acetonide compound is obtained from the reaction of D-methyl tartrate and 2,2-dimethoxypropane in the presence of para-toluenesulfonic acid in dichloromethane.

(3) 2,3-O-Isopropylidene-D-threitol is obtained from the reduction of 4,5-dimethoxycarbonyl acetonide with sodium borohydride in methanol.

(4) 2,3-O-Isopropylidene-D-threitol is treated with triethylamine, lithium halide, and methanesulfonyl halide in acetonitrile to yield 1,4-dihalobutane-2(S),3(S)-diol.

(5) 1,4-Dihalobutane-2(S),3(S)-diol sulfate is prepared from the reaction of 1,4-dihalobutane-2(S),3(S)-diol with either thionyl chloride in chloroform followed by oxidation using ruthenium chloride and sodium periodate, or imidazole sulfuryl chloride in carbon tetrachloride.

(6) 1,4-Dihalobutane-2(S),3(S)-diol sulfate is treated with potassium phthalimide in DMF to provide N-[1,4-dihalo-2(S)-hydroxy-3(R)-butyl]phthalimide.

(7) N-[1,4-Dihalo-2(S)-hydroxy-3(R)-butyl]phthalimide was treated with 80% hydrazine monohydrate in isopropanol to remove the phthalimide protecting group and the resulting free amine was converted to 2(R)-(alkyloxycarbonyl)amino-1,4-dihalo-3(S)-hydroxybutane upon reaction with an acid anhydride in presence of triethylamine in tetrahydrofuran (THF).

(8) Reaction of 2(R)-(alkyloxycarbonyl)amino-1,4-dihalo-3(S)-hydroxybutane with hydroxyl protecting groups such as chlorosilane or chlorocarbonyl group provides 2(S)-silyl(or carbonyl)oxy-3(R)-alkyloxycarbonylamino-1,4-dihalobutane.

(9) N-alkyloxycarbonyl-2(R)-[1(S)-silyloxy-2-haloethyl] aziridine is prepared from the reaction of 2(S)-silyl(or carbonyl)oxy-3(R)-alkyloxycarbonylamino-1,4-dihalobutane with sodium hydride in THF.

Above preoaration method is depicted in Scheme (1-a).

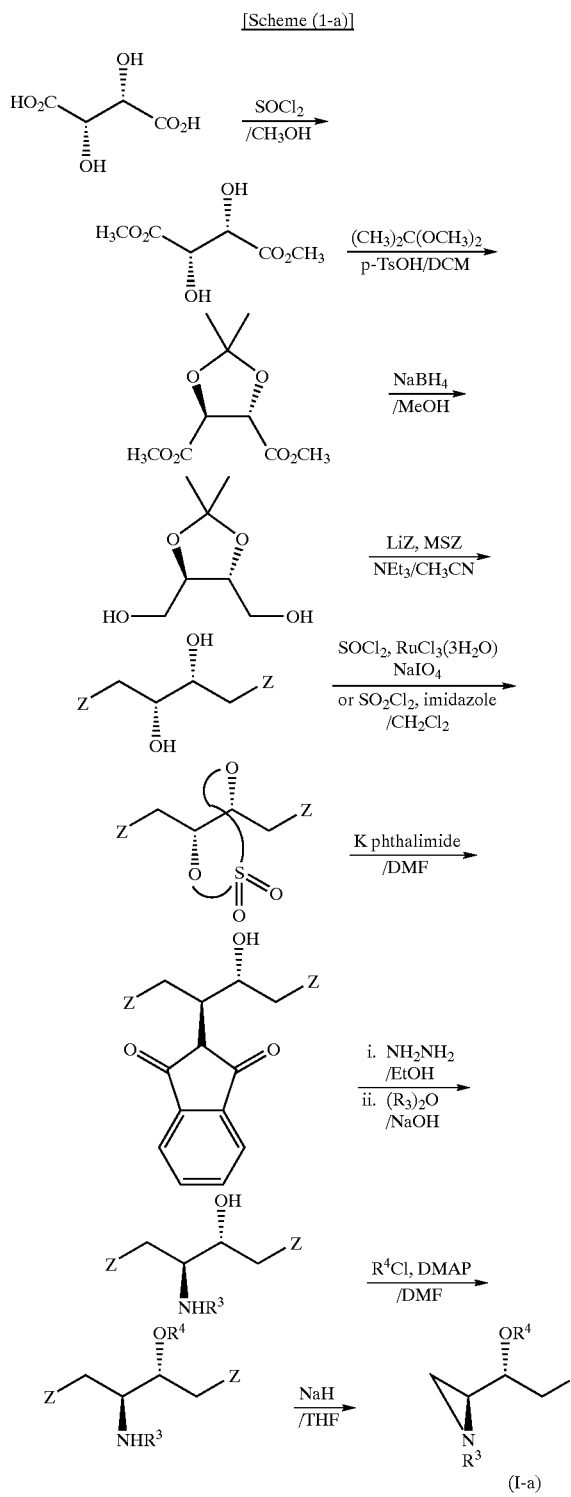

When the same sequence is repeated starting from L-tartaric acid, the following compound of general formula (I-b) can be prepared.

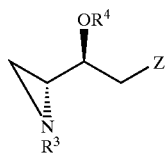

Two isomers of formula (I-a) arnd formula (I-b) are depicted as formula (I') as below.

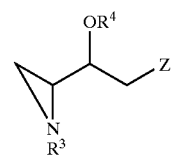

This invention also provides the following compound of general formula (II).

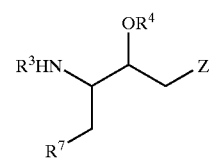

wherein:

$R_3$ is H, alkyl, aryl, arylaikyl, or amino protecting group forming $C_{5-7}$ monocyclic heterocycle or $C_{7-11}$ bicyclic heterocycle with nitrogen atom;

$R_4$ is silyl protecting group optionally substituted with alkyl group, or alcohol protecting group which includes alkoxycarbonyl, aryloxycarbonyl, methoxymethyl, tetrahydropyranyl, methoxyethoxy methyl or ethoxyvinylethyl;

Z is F, Cl, Br, I, or —$OSO_nR_5$ where n=0, 1 or 2, and $R_5$ is alkyl or aryl; and $R_7$ is phenyl, phenyl substituted with hydroxy, halogen, alkyl or alkoxy group at the para position, phenylthio, pyridyl, piperidyl, cyclohexyl, $C_{1-4}$ alkyl, alkenyl, or alkenyl substituted with phenyl.

Compound of general formula (II) is prepared from ethylaziridine derivative of general formula (I') by the following reaction.

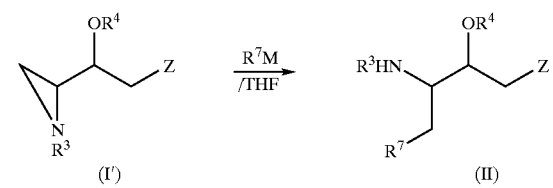

In the above reaction, $R_3$, $R_4$, Z, and $R_7$ are same as defined above and M is alkali metal or alkali earth metal halide.

Also this invention provides new compounds of the following formula (III).

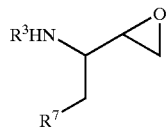

wherein,

R₃ is H, alkyl, aryl, arylakyl, or amino protecting group forming $C_{5-7}$ monocyclic heterocycle or $C_{7-11}$ bicyclic heterocycle with nitrogen atom; and R₇ is phenyl, phenyl substituted with hydroxy, halogen, alkyl or alkoxy group at the para position, phenylthio, pyridyl, piperidyl, cyclohexyl, $C_{1-4}$ alkyl, alkenyl, or alkenyl substituted with phenyl.

Compounds of general formula (III) are prepared from compounds of general formula (II) by the reaction with tetrabutylammonium fluoride (TBAF).

[Scheme 3]

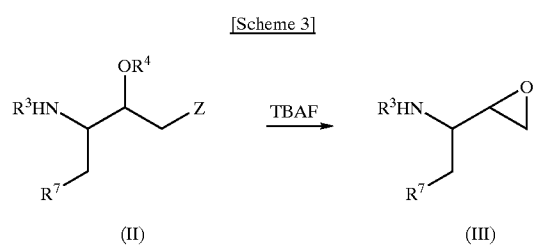

Also afore-mentioned Amprenavir and Nelfinavir can be prepared from compound formula (II) and formula (III) through reactions of Scheme 4 and Scheme 5, respectively. Compounds of formula (II) and (III) are synthetic intermediates for Amprenavir when R₇ is phenyl, and for Nelfinavir when R₇ is phenylthio group, respectively.

[Scheme 4]

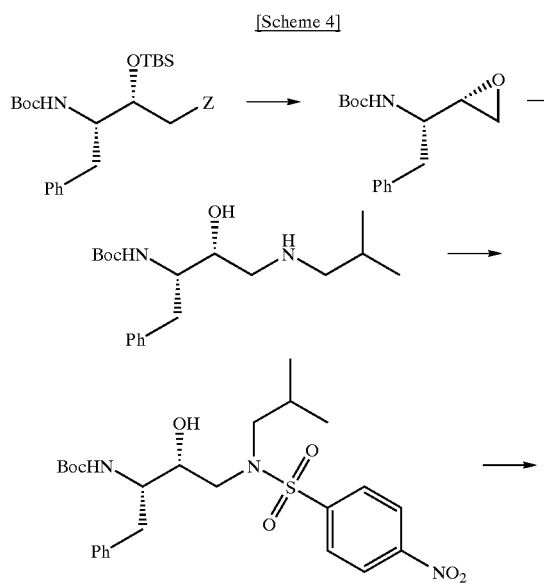

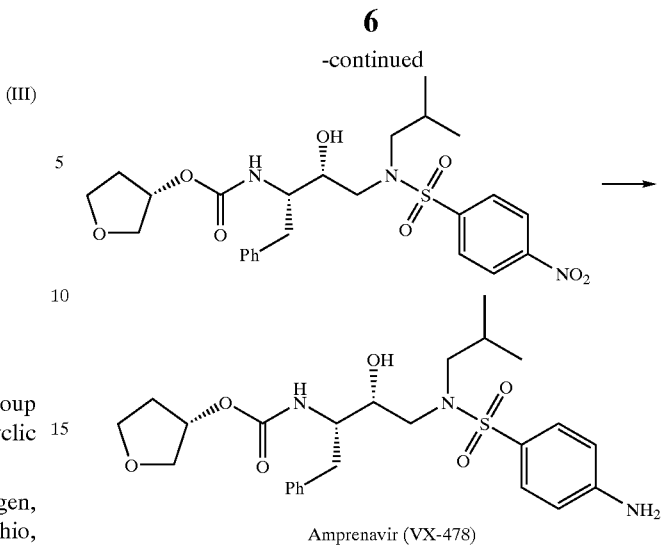

Amprenavir (VX-478)

[Scheme 5]

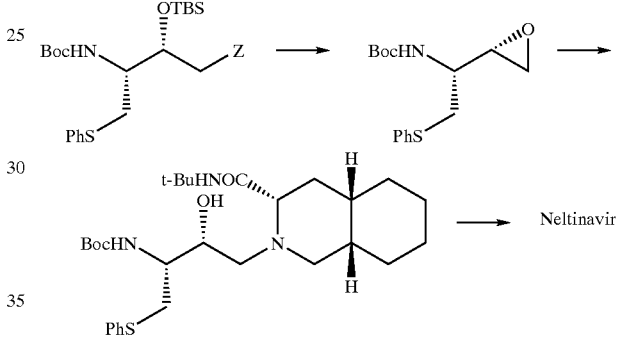

→ Neltinavir

This invention is explained more in detail through examples below.

Synthesis of Ethylaziridine Derivatives from D-tartaric Acid

EXAMPLE 1

Preparation of dimethyl D-tartrate

To a solution of D-tartaric acid (19.1 g, 127 mmol) in anhydrous methanol (60 mL) was slowly added thionyl chloride (48.3 mL, 665 mmol) at 0° C. After an hour, the reaction mixture was heated to reflux for 3 hours, to give pale yellow solution. Gaseous hydrogen chloride and methanol solvent were removed under reduced pressure. After the extraction of water solution (40 mL) with ethyl acetate (40 mL×8), ethyl acetate solution was dried over anhydrous $MgSO_4$, filtered, and concentrated to give pale yellow oil (22.5 g, 126 mmol).

$^1$H NMR (300 MHz, $CDCl_3$) δ3.40~3.42 (bs, 1H), 3.87 (s, 3H), 4.57 (s, 1H)

EXAMPLE 2

Preparation of 2,3-O-isopropylidene-D-tartrate

To a solution of dimethyl ester of L-tartaric acid (22.5 g, 126 mmol) in anhydrous dichloromethane (300 mL) were added p-toluenesulfonic acid monohydrate (12.0 g, 63.0 mmol) and 2,2-dimethoxypropane (101 mL, 825 mmol) at room temperature. Then the reaction mixture was heated to reflux for 4 hours, and was concentrated under reduced pressure. After the extraction of water solution (40 mL) with ethyl acetate (100 mL), ethyl acetate solution was dried over anhydrous $MgSO_4$, filtered, and concentrated to give reddish oil (24.1 g, 124 mmol).

$^1H$ NMR (300 MHz, $CDCl_3$) δ1.50 (s, 6H), 3.83 (s, 6H), 4.82 (s, 2H)

EXAMPLE 3

Preparation of 2,3-O-isorropylidene-D-threitol

To a solution of 2,3-O-isopropylidene-D-tartrate (24.0 g, 124 mmol) in anhydrous methanol (400 mL) was slowly added anhydrous sodium borohydride (23.4 g, 618 mmol) at 0° C., which was spontaneously raised to room temperature. After the reaction mixture was stirred for 4 hours, it was concentrated under reduced pressure. Then the mixture was transferred to a separatory funnel, and distilled water (400 mL) was added. After extraction with ethyl acetate (400 mL×4), the solution was dried over anhydrous $MgSO_4$, filtered, and concentrated to give pale yellow oil (17.2 g, 106 mmol).

$^1H$ NMR (300 MHz, $CDCl_3$) δ1.44 (s, 6H), 2.52 (br s, 2H), 3.69~3.82 (m, 4H), 4.00~4.01 (m, 2 H)

EXAMPLE 4

Preparation of 1,4-dichlorobutane-2(S),3(S)-diol

To a solution of 2,3-O-isopropylidene-D-threitol (17.2 g, 106 mmol) in acetonitrile (300 mL) was added triethylamine (34.0 mL, 244 mmol), lithium chloride (40.0 g, 944 mmol), and methanesulfonyl chloride (17.3 mL, 224 mmol) in sequence at 0 C. After being stirred for 30 minutes, the reaction mixture was heated to reflux overnight. Then the acidic mixture was concentrated under reduced pressure and was extracted with ethyl acetate (500 mL×2) from aqueous sodium bicarbonate solution. After being dried over anhydrous $MgSO_4$, the mixture was filtered and concentrated to give dark brown liquid. The nonpolar dark brown impurity was extracted and separated from the liquid by water (200 mL) with n-hexane (200 mL). After extraction of the water solution with ethyl acetate (200×4 mL), the ethyl acetate solution was dried over anhydrous $MgSO_4$, filtered, and concentrated to give white crystalline solid (8.35 g, 52.5 mmol).

$^1H$ NMR (300 MHz, $CDCl_3$) δ2.58 (bs, 2H), 3.64~3.76 (m, 4H), 3.96~3.98 (m, 2H); $^{13}C$ NMR (75 MHz, $CDCl_3$) δ45.85, 71.02.

EXAMPLE 5

Preparation of 1,4-dichlorobutan-2(S),3(S)-diol sulfate

Method A

To 1,4-dichlorobutan-2(S),3(S)-diol (159 mg, 1.0 mmol) in $CCl_4$ (1 mL) was added thionyl chloride (88 μl, 1.2 mmol) via a syringe and the resulting solution was refluxed for 30 min. The reaction mixture was concentrated by rotary evaporation, the residue was pumped under reduced pressure for 1 h, and to this residue was added a cold solution of $CCl_4$ (3 mL) and $CH_3CN$ (3 mL). The flask was cooled in an ice bath and cold water (4.5 mL) was added. $RuCl_3.H_2O$ (1.15 mg, 0.01 mmol) and $NaIO_4$ (0.428 g, 2.0 mmol) were added at once and the reaction mixture was stirred vigorously at 0°C. After 1 hour stirring, ether (6 mL) was added and the layers were separated. The aqueous layer was extracted with ether (2.5 mL×3). The combined organic layers were washed with brine (3 mL), dried over anhydrous $MgSO_4$ and concentrated to give 206.4 mg as a white solid.

$R_f$ (silica gel; 33% EtOAc in n-Hex) 0.65

$[α]_D^{25}$ =+57.5 (c 1.02, MeOH)

$^1H$ NMR (200 MHz, $CDCl_3$) δ5.02 (2H, m), 3.93 (4H, m)

$^{13}C$ NMR (125 MHz, $CDCl_3$) δ81.15, 41.73.

IR (KBr pellet) 2979, 1384, 1209, 1021, 985, 896, 653 $cm^{-1}$

Method B

Sulfuryl chloride (0.104 mL, 1.258 mmol) was added dropwise to a solution of 1,4-dichloro-2,3-butanediol (100.3 mg, 0.631 mmol) and imidazole (85.8 mg, 1.26 mmol) in $CH_2Cl_2$ (2.1 mL) at 27° C. A precipitate formed gradually upon addition. When the addition was complete, the mixture was stirred at the same temperature. When the reaction was complete, the mixture was diluted with $CH_2Cl_2$ (2.5 mL). Sulfuric acid (5% aq. 0.75 mL) was added to the mixture and layers were separated. The organic phase was washed with sat. aq. $NaHCO_3$ (0.75 mL) and brine, dried over anhyd $MgSO_4$, and concentrated under reduced pressure to give 98.1 mg (70.3% yield).

EXAMPLE 6

Preparation of N-(1,4-Dichloro-2(S)-hydroxy-3(R)-butyl)phthalimide

A mixture of 1,4-dichlorobutan-2(S),3(S)-diol sulfate (57.2 mg, 0.258 mmol) and phthalimide potassium salt (51.4 mg, 0.272 mmol) in dry DMF (1.3 mL) was stirred under nitrogen atmosphere at rt for 1 h. Solvent was removed under reduced pressure. The residue was dissolved with dry THF (3 mL). To the resulting solution were added conc. $H_2SO_4$ (13 μl) and water (5 μl). After 30 min excess sodium bicarbonate (~52 mg) was added and the reaction mixture was stirred for 30 min. Filtration through a Celite and silica gel bed and concentration of the filtrate under reduced pressure provided N-(1,4-Dichloro-2(S)-hydroxy-3(R)-butyl)phthalimide (77.8 mg) as a colorless oil.

$^1H$ NMR (300 MHz, $CDCl_3$) δ8.02~7.72 (4H, m), 4.68~4.60 (1H, m), 4.56~4.47 (1H, m), 4.25 (1H, dd, J=10.81, 11.55), 4.10 (1H, dd, J=4.13, 11.64), 3.67 (1H, dd, J=3.93, 11.65), 3.58 (1H, dd, J=5.81, 11.64), 3.06 (1H, d, J=5.21).

$^{13}C$ NMR (75 MHz, $CDCl_3$) 168.27, 134.65, 134.41, 131.42, 123.89, 123.69, 70.51, 55.25, 47.33, 41.80.

EXAMPLE 7

Preparation of 2(R)-(t-Butyloxycarbonyl)amino-1,4-dichloro-3(S)-hydroxy butane

To a solution of N-(1,4-dichloro-2(S)-hydroxy-3(R)-butyl)phthalimide (48.6 mg, 0.169 mmol) in isopropanol (1 mL) was added 80% hydrazine monohydrate (11.3 L, 0.187 mmol) at 0° C. under $N_2$. After 16 h, solvent was removed under reduced pressure. The resulting solid was dissolved with MeOH (1 mL). To the reaction mixture was added 35% HCl (21.0 μl, 0.240 mmol) at rt. After 16 h, solvent was removed under reduced pressure. The residue was dissolved with THF (0.5 mL) and water (0.5 mL). To the reaction mixture was added $(Boc)_2O$ (46.5 mg, 0.213 mmol) and $NEt_3$ (49.5 L, 0.355 mmol) at 0° C. After 16 h, the reaction mixture was diluted with water (1 mL) and extracted with EtOAc (2 mL×3). The combined organic layers were washed with brine (1 mL), dried over anhydrous magnesium sulfate, and filtered. The filtrate was concentrated under reduced pressure and column chromatography (25% EtOAc in n-Hex) gave 2(R)-(t-butyloxycarbonyl)amino-1,4-dichloro-3(S)-hydroxybutane (32.7 mg) as a white solid.

Yield: 75% yield mp: 142–145° C.

$[\alpha]_D^{23}$ =+29.8 (c 1.00, MeOH)

$^1$H-NMR (300 MHz, CDCl$_3$) δ4.78 (1H, br d), 3.96~3.82 (1H, m), 3.82~3.63 (1H, m), 3.60~3.50 (2H, m) 3.44 (1H, dd, J=7.14, 11.27), 2.56(1H, bs), 1.26 (9H, s)

$^{13}$C NMR (75 MHz, CDCl$_3$) δ155.3, 80.5, 71.2, 53.0, 48.0, 45.8, 28.3

IR (KBr pellet) 3450, 3357, 2982, 1682, 1519, 1344, 1168, 1010, 597 cm$^{-1}$ mp 142~145° C.

HRMS (Cl) m/z calcd 258.0664 for [M+H]$^+$ C$_9$H$_{18}$NO$_3$Cl$_2$ found 258.0669.

EXAMPLE 8

Preparation of 2(S)-t-Butyldimetylsilyloxy-3(R)-(t-butyloxycarbonyl)amino-1,4-dichlorobutane To a stirred solution of 2(R)-(t-butyloxycarbonyl)amino-1,4-dichloro-3(S)-hydroxybutane (100.0 mg, 0.389 mmol) in dry DMF (2.5 mL) were added imidazole (79.4 mg, 1.67 mmol), DMAP (4.8 mg, 0.039 mmol) and TBS-Cl (175.9 mg, 1.167 mmol) at room temperature under N$_2$. The resulting solution was stirred at 50° C. for 12 h. The reaction mixture was diluted with EtOAc (30 mL), washed with 0.1 N citric acid solution (5 mL), sat aqueous NaHCO$_3$ (5 mL), water (5 mL) and brine (5 mL), dried over anhydrous magnesium sulfate, filtered, concentrated and column-chromatographed (10% EtOAc in n-Hex) to provide 2(S)-t-butyldimetylsilyloxy-3(R))-(t-butyloxycarbonyl)amino-1,4-dichlorobutane as a colorless solid (144.6 mg)

Yield: 99.4%

Rf 0.52 (silica gel, 10% EtOAc in n-Hex)

$^1$H-NMR (300 MHz, CDCl$_3$) δ4.84~4.81 (1H, bd), 4.12~4.04 (1H, m), 4.03~3.93 (1H, m), 3.87 (1H, dd, J=4.7, 11.16), 3.68 (1H, dd, J=3.46, 11.15), 3.60 (2H, d), 1.45 (9H, s), 0.90 (9H, s), 0.14 (3H, s), 0.13 (3H, s).

EXAMPLE 9

Preparation of N-t-Butyloxycarbonyl-2(R)-(1(S)-t-butyldimetysilyloxy-2-chloroethyl)aziridine To a magnetically stirred solution of 2(S)-t-butyldimethylsilyloxy-3(R)-(t-butyloxycarbonyl)amino-1,4-dichlorobutane (375.4 mg, 1.008 mmol) in THF (10 mL) was added NaH slowly at 0° C. under N$_2$. After 5 h, the reaction mixture was slowly added to sat aq ammonium chloride solution (40 mL) and ice (20 g). The resulting solution was extracted with EtOAc (60 mL 4). The combined organic layers were washed with brine (50 mL), dried over anhydrous magnesium sulfate, filtered, concentrated and column chromatographed (10% EtOAc in n-Hex) to provide N-t-butyloxycarbonyl-2(R)-(1(S)-t-butyldimetylsilyloxy-2-chloroethyl)aziridine (339.5 mg) as a colorless oil.

Yield: 99%

Rf 0.60 (silica gel, 10% EtOAc in n-Hex)

H-NMR (300 MHz, CDCl$_3$) δ3.69 (1H, dd, J=3.92, 11.10), 3.68 (1H, dd, J=6.08, 11.09), 3.53 (1H, ddd, J=3.95, 6.20, 6.15), 2.51 (1H, m, J=3.62, 6.21, 6.24), 2.33 (1H, d, J=6.13), 2.07 (1H, d, J=3.59), 1.44(9H, s), 0.89 (9H, s), 0.09 (3H, s), 0.06 (3H, s)

$^{13}$C NMR (75 MHz, CDCl3) δ161.92, 8.37, 73.38, 47.84, 39.34, 30.10, 27.85, 25.68, 18.12, −4.51, −4.84.

EXAMPLE 10

Preparation of 2(S)-t-Butyldimetylsilyloxy-3(S)-(t-butyloxycarbonyl)amino-1-chloro-4-phenylbutane To a magnetically stirred solution of N-t-butyloxycarbonyl-2(R)-(1(S)-t-butyldimetylsilyloxy-2-chloroethyl)aziridine (36.0 mg, 0.107 mmol) in toluene was added copper bromide dimethyl sulfide complex (11.0 mg, 0.054 mmol) at rt under N$_2$. The reaction mixture was cooled to −78° C. then treated with a 2 M solution of PhMgCl in THF (0.54 mL, 1.072 mmol). The resulting mixture was warmed to −20° C. and stirred overnight. The reaction mixture was treated with sat NH$_4$Cl (4 mL) and extracted with EtOAc(5 mL×3). The combined organic layers were washed with brine (50 mL), dried over anhydrous magnesium sulfate, filtered, concentrated and column-chromatographed (3% EtAc in n-Hex) to provide 2(S)-t-butyldimetylsilyloxy-3(R)-(t-butyloxycarbonyl)amino-1-chloro-4-phenylbutane (33.5 mg) as a colorless oil.

Yield: 75%

$^1$H-NMR (300 MHz, CDCl$_3$) δ7.31~7.19 (H, m), 4.46 (1H, d, J=7.44), 4.16~4.01 (2H, m), 3.52~3.41 (2H, m), 2.96 (1H, dd, J=4.32, 14.19), 2.66 (1H, dd, J=10.61, 13.55), 1.33 (9H, s), 0.94 (9H, s), 0.13 (3H, s), 0.12 (3H, s)

$^{13}$C NMR (75 MHz, CDCl$_3$) δ155.06, 138.16, 129.22, 128.39, 126.34, 79.32, 74.15, 53.83, 45.53, 34.23, 28.26, 25.84, 18.14, −4.31, −4.76.

EXAMPLE 11

Preparation of 3(S)-(t-Butyloxycarbonyl)amino-1,2(S)-epoxy-4-phenylbutane

To a magnetically stirred solution of 2(S)-t-butyldimetylsilyloxy-3(R)-(t-butyloxycarbonyl)amino-1-chloro-4-phenylbutane (30.0 mg, 0.073 mmol) in THF (0.5 mL) was added a 1 M solution of TBAF in THF (0.11 mL, 0.109 mmol) at 0° C. After 10 min, stirring was continued at room temperature for 40 min. The reaction mixture was treated with sat NH$_4$Cl (0.5 mL), diluted with water (2 mL), and extracted with EtOAc (3 mL×3). The combined organic layers were washed with brine (3 mL), dried over anhyd magnesium sulfate, filtered, and concentrated. The residue was dissolved with MeOH (0.5 mL) and treated with KOH at 0° C. Stirring was continued at room temperature for 2 h. Solvent was removed under reduced pressure, diluted with water (2 mL), and extracted with EtOAc (3 mL×3). The combined organic layers were washed with brine (3 mL), dried over anhydrous magnesium sulfate, filtered, concentrated and column-chromatographed (10% EtOAc in n-Hex) to provide 3(S)-(t-butyloxycarbonyl)amino-1,2(S)-epoxy-4-phenylbutane (14.4 mg) as a white solid.

Yield: 75%

$^1$H-NMR (300 MHz, CDCl$_3$) δ7.35~7.22 (5H, m), 4.46 (1H, bs), 3.70 (1H, bs), 2.98 (1H, dd, J=5.16, 14.00), 2.90 (1H, m), 2.85~2.79 (1H, m), 2.78~2.73 (1H, m), 1.38 (9H, s)

$^{13}$C NMR (75 MHz, CDCl$_3$) δ155.20, 136.66, 129.44, 128.54, 126.67, 79.64, 53.18, 52.58, 46.91, 37.58, 28.25.

Synthesis of Amprenavir from Ethylaziridine Derivative

EXAMPLE 12

Preparation of 2(S)-hydroxy-3(S)-(t-butyloxycarbonyl)amino-1-isobutylamino-4-phenylbutane To a solution of 3(S)-(t-butyloxycarbonyl)amino-1,2(S)-epoxy-4-phenylbutane (200 mg, 0.76 mmol) in 2 mL of dry isopropanol was added isobutylamine (0.38 mL, 3.8 mmol) and the mixture was stirred for 5 h at 50° C. The mixture was concentrated under reduced pressure and dried in vaccuo to give 230 mg of 2(S)-hydroxy-3(S)-(t-butyloxycarbonyl)amino-1-isobutylamino-4-phenylbutane Yield: 90%

$[\alpha]_D^{26}$=8.9 (c1.0, CHCl$_3$)

$^1$H NMR (300 MHz, CDCl$_3$) δ0.91 (d, J=6.6 Hz, 6H), 1.36 (s, 9H), 1.68~1.78 (m, 2H), 2.42 (d, J=6.6 Hz, 2H), 2.83~3.03 (m, 5H), 3.45~3.47 (m, 1 H), 3.82 (br, 1H), 4.68 (br, 1H), 7.22~7.32 (m, 5H).

EXAMPLE 13

Preparation of 2(S)-hydroxy-3(S)-(t-butyloxycarbonyl)amino-1-(4-nitrobenzenesulfonyl)-1-isobutylamino-4-phenylbutane To a solution of 2(S)-hydroxy-3(S)-(t-butyloxycarbonyl)amino-1-isobutyl amino-4-phenylbutane (64 mg, 0.19 mmol) in 1 mL of dry CH$_2$Cl$_2$ were added triethylamine (30 μl, 0.23 mmol) and 4-nitrobenzensulfonyl chloride (55 mg, 0.25 mmol) at 0° C. The mixture was stirred for 30 min at this temperature and the flask was warmed to room temperature. The mixture was stirred for 12 h at room temperature and poured into sat aq NaHCO$_3$ solution (2 mL) and extracted with Et$_2$O (10 mL). The organic extract was dried over anhydrous MgSO$_4$ and concentrated. Silica gel column chromatography provided 82 mg of 2(S)-hydroxy-3(S)-(t-butyloxycarbonyl)amino-1-(4-nitrobenzenesulfonyl)-1-isobutylamino-4-phenylbutane.

Yield: 88%

$^1$H NMR (300 MHz, COCl$_3$) δ0.86~0.89 (m, 6H), 1.36 (s, 9H), 1.83~1.93 (m, 1H), 2.89~3.00 (m, 4H), 3.19~3.21 (m, 2H), 3.76~3.85 (m, 3H), 4.64 (br, 1H), 7.22~7.34 (m, 5H), 7.96 (d, J=8.7 Hz, 2H), 8.34 (d, J=8.7 Hz, 2H).

EXAMPLE 14

Preparation of 2(S)-hydroxy-3(S)-[3(S)-tetrahydropyranyloxycarbonyl]amino-1-(4-nitrobenzenesulfonyl)-1-isobutylamino-4-phenylbutane To a solution of 2(S)-hydroxy-3(S)-(t-butyloxycarbonyl)amino-1-(4-nitrobenzenesulfonyl)-1-isobutylamino-4-phenylbutane (93 mg, 0.19 mmol) in 1 mL of dry CH$_2$Cl$_2$ was passed anhydrous HCl gas for 0.5 h. After removal of HCl gas bubbler, the mixture was stirred for 1 h. The solvent was removed in vaccuo and the residue was dissolved in 1 mL of dry CH$_2$Cl$_2$. To the mixture were added triethylamine (30 μl, 0.23 mmol) and N-succinimidyl (S)-(+)-3-hydroxytetrahydrofuran carbonate (44 mg, 0.19 mmol) at room temperature. The mixture was stirred for 4 h until no starting material remained by TLC and it was poured into brine (2 mL) and extracted with EtOAc (10 mL). The organic extract was dried over anhydrous MgSO$_4$ and concentrated under reduced pressure. The crude compound was recrystallized in ethyl acetate to give 86 mg of 2(S)-hydroxy-3(S)-[3(S)-tetrahydropyranyloxycarbonyl]amino-1-(4-nitrobenzenesulfonyl)-1-isobutylamino-4-phenylbutane.

Yield: 85%

$^1$H NMR (300 MHz, CDCl$_3$) δ0.86~0.91 (m, 6H), 1.65~1.95 (m, 2H), 2.08~2.21 (m, 1H), 2.85~3.02 (m, 4H), 3.05~3.24 (m, 2H), 3.63~3.68 (m, 2H), 3.76~3.87 (m, 5H), 4.89 (br, 1H), 5.14 (br, 1H), 7.14~7.35 (m, 5H), 7.96 (d, J=8.7 Hz, 2H), 8.36 (d, J=8.7 Hz, 2H)

EXAMPLE 15

Preparation of 2(S)-hydroxy-3(S)-[3(S)-tetrahydropyranyloxycarbonyl]amino-1-(4-aminobenzenesulfonyl)-1-isobutylamino-4-phenylbutane A mixture of 2(S)-hydroxy-3(S)-[3(S)-tetrahydropyranyloxycarbonyl]amino-1-(4-nitrobenzenesulfonyl)-1-isobutylamino-4-phenylbutane (36 mg, 0.067 mmol) and SnCl$_2$.2H$_2$O (77 mg, 0.34 mmol) in 1 mL of EtOAc was heated to 70° C. After 1 h the starting material disappeared and the solution was allowed to cool to room temperature. The mixture was poured into sat aq NaHCO$_3$ solution (3 mL) and extracted with EtOAc (10 mL). The organic extract was dried over anhyd MgSO$_4$ and concentrated under reduced pressure to give 30 mg of 2(S)-hydroxy-3(S)-[3(S)-tetrahydropyranyloxycarbonyl]amino-1-(4-aminobenzenesulfonyl)-1-isobutylamino-4-phenylbutane.

Yield: 90%

$^1$H NMR (300 MHz, CDCl$_3$) δ0.85~0.92 (m, 6H), 1.78~2.21 (m, 3H), 2.72~3.11 (m, 6H), 3.58~4.11(m, 7H), 4.20 (s, 2H) 4.93 (br, 1H), 5.11 (br, 1H), 6.67 (d, J=8.6 Hz, 2H), 7.22~7.32 (m, 5H), 7.54 (d, J=8.6 Hz, 2H)

Newly synthesized N-t-Butyloxycarbonyl-2(R)-(1(S)-t-butyldimetylsilyloxy-2-chloroethyl)aziridine can be utilized as an important intermediate for the synthesis of Amprenavir and Nelfinavir among HIV protease inhibitor molecules. Introduction of phenyl group by opening of the aziridine ring leads to the preparation of 3(S)-(t-butyloxycarbonyl)amino-1,2(S)-epoxy-4-phenylthiobutane, which is a core intermediate for the synthesis of Amprenavir. Introduction of phenylthio group insead of the phenyl one allows for the synthesis of 3(S)-(t-butyloxycarbonyl)amino-1,2(S)-epoxy-4-phenylbutane, which is a core intermediate for the synthesis of Nelfinavir. N-t-Butyloxycarbonyl-2(S)-(1(R)-t-butyldimetylsilyloxy-2-chloroethyl)aziridine, which is an enantiomer of above compound can be utilized as an intermediate for the synthesis of the stereochemical antipode of the HIV protease inhibitors possessing hydroxyethylamine backbone.

What is claimed is:

1. An ethylaziridine derivative of the formula (I')

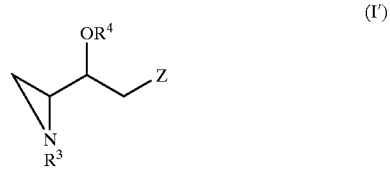

wherein,

R$_3$ is selected from the group consisting of H, alkyl, aryl, arylakyl, an amino protecting group forming a C$_{5-7}$ monocyclic heterocycle with the N atom, and an amino protecting group forming a C$_{7-11}$ bicyclic heterocycle with the N atom;

R$_4$ is a silyl proticting group optionally substituted with alkyl or an alcohol protecting group selected from the group consisting of alkoxycarbonyl, aryloxycarbonyl, methoxymethyl, tetrahydropyranyl, methoxyethoxy methyl or ethoxyvinylethyl;

Z is F, CI, Br, I, or —OSO$_n$R$_5$, where n=0, 1, or 2, and R$_5$ is alkyl or aryl.

2. A process for the preparation of compound of the formula (I')

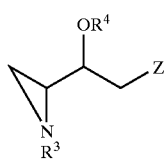

(I')

where $R_3$ is H, alkyl, aryl, arylakyl, or amino protecting group forming $C_{5-7}$ monocyclic heterocycle or $C_{7-11}$ bicyclic heterocycle with nitrogen atom; $R_4$ is a silyl protecting group optionally substituted with alkyl, or alcohol protecting group selected from the group consisting of alkoxycarbonyl, aryloxycarbonyl, methoxymethyl, tetrahydropyranyl, methoxyethoxymethyl or ethoxyvinylethyl; and Z is F, Cl, Br, I, or —$OSO_nR_5$, where n=0, 1 or 2, and $R_5$ is alkyl or aryl, which comprises (a) reacting 1,4-dihalobutanediol sulfate with potassium phthalimide to produce N-[1,4-dihalo-2-hydroxy-3-butyl]phthalimide;

(b) converting an amine generated from the deprotection of the phthalimide group of N-[1,4-dihalo-2-hydroxy-3-butyl]phthalmide to 2-(t-alkyloxycarbonyl)amino-1,4-dihalo-3-hydroxybutane;

(c) reacting 2-(t-alkyloxycarbonyl)amino-1,4-dihalo-3-hydroxybutane with chlorosilane or chlorocarbonyl to produce 2-silyl(or carbonyl)oxy-3-(alkyloxycarbonyl)amino-1,4-dihalobutane; and (d) converting 2-silyl(or carbonyl)oxy-3-(alkyloxycarbonyl)amino-1,4-dihalobutane to N-t-alkyloxycarbonyl-2-[1-t-silyl(carbonyl)oxy-2-haloethyl)aziridine.

* * * * *